United States Patent
Bohlin et al.

(10) Patent No.: US 8,124,779 B2
(45) Date of Patent: Feb. 28, 2012

(54) PROCESS FOR THE PREPARATION OF ESOMEPRAZOLE NON-SALT FORM

(75) Inventors: Martin Bohlin, Södertälje (SE); Per Lindberg, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 785 days.

(21) Appl. No.: 12/096,199

(22) PCT Filed: Dec. 4, 2006

(86) PCT No.: PCT/SE2006/001381

§ 371 (c)(1),
(2), (4) Date: Jun. 5, 2008

(87) PCT Pub. No.: WO2007/067128

PCT Pub. Date: Jun. 14, 2007

(65) Prior Publication Data

US 2008/0269297 A1    Oct. 30, 2008

Related U.S. Application Data

(60) Provisional application No. 60/742,296, filed on Dec. 5, 2005.

(51) Int. Cl.
C07D 401/12 (2006.01)
(52) U.S. Cl. .................................................. 546/273.7
(58) Field of Classification Search ................ 546/273.7
See application file for complete search history.

(56) References Cited

FOREIGN PATENT DOCUMENTS

CN    1467207    1/2004
(Continued)

OTHER PUBLICATIONS

Kirk-Othmer Encyclopedia of Chemical Technology, vol. 8, p. 95-147 (2002).*

*Primary Examiner* — Patricia Morris
(74) *Attorney, Agent, or Firm* — White & Case LLP

(57) ABSTRACT

The present invention relates to a new process for the preparation of new crystal modifications of esomeprazole non-salt form. Further, the present invention also relates to the use of said new crystal modifications for the treatment of gastrointestinal disorders, pharmaceutical compositions containing them as well as the crystal modifications, as such.

7 Claims, 4 Drawing Sheets

FOREIGN PATENT DOCUMENTS

| | | |
|---|---|---|
| EP | 5129 | 4/1981 |
| EP | 247983 | 1/1993 |
| WO | WO 94/27988 | 12/1994 |
| WO | WO 96/01623 | 1/1996 |
| WO | WO 96/02535 | 2/1996 |
| WO | WO 98/28294 | 7/1998 |
| WO | WO 98/28299 | 7/1998 |
| WO | WO 2004/037253 | 5/2004 |
| WO | WO 2004/072061 | 8/2004 |
| WO | WO 2004/076440 | 9/2004 |

\* cited by examiner

PROCESS FOR THE PREPARATION OF ESOMEPRAZOLE NON-SALT FORM This application claims the benefit of U.S. provisional patent application Ser. No. 60/742,296, filed Dec. 5, 2005.

FIELD OF THE INVENTION

The present invention relates to a new process for the preparation of esomeprazole non-salt form. Further, the present invention also relates to new crystal modifications prepared in said process, the use of said new crystal modifications for the treatment of gastrointestinal disorders, as well as pharmaceutical compositions containing them.

BACKGROUND OF THE INVENTION AND PRIOR ART

Omeprazole, i.e. the compound 5-methoxy-2-[[(4-methoxy-3,5-dimethyl-2-pyridinyl)methyl]sulfinyl]-1 H-benzimidazole, and therapeutically acceptable salts thereof, are described in EP 5129.

Omeprazole is a sulfoxide and a chiral compound, wherein the sulfur atom is the stereogenic center. Thus, omeprazole is a racemic mixture of its two single enantiomers, the R- and S-enantiomer of omeprazole, the latter having the generic name esomeprazole. Esomeprazole (Nexium™) is a new generation of proton pump inhibitors, wherein the active pharmaceutical ingredient is esomeprazole magnesium salt. The esomeprazole sodium salt is commercially available for i.v. administration. Nexium™ shows improvements in the treatment of GERD compared to previous medications.

The absolute configurations of the enantiomers of omeprazole have been determined by an X-ray study of an N-alkylated derivative of the (+)-enantiomer in non-salt form. The (+)-enantiomer of the non-salt form and the (−)-enantiomer of the non-salt form were found to have R and S configuration, respectively. The conditions for the optical rotation measurement for each of these enantiomers are described in WO 94/27988.

Certain salts of single enantiomers of omeprazole and their preparation are also disclosed in WO 94/27988. These compounds have improved pharmacokinetic and metabolic properties, which will give an improved therapeutic profile, such as a lower degree of interindividual variation.

WO 96/02535 discloses a process for the preparation of the single enantiomers of omeprazole and salts thereof.

WO 98/28299 discloses solid-state forms of esomeprazole non-salt form prepared from the corresponding sodium salt either by crystallization from an organic solvent (Form A) or by reaction crystallization from a water/acetone mixture (Form B). Form B is said to be a less crystalline form.

WO 04/076440 (Ranbaxy) discloses two polymorphic forms of esomeprazole non-salt form denoted Form I and Form II.

CN1467207A (China Academy Sci Chengdu Inst Organic Chem) discloses a process for the preparation of solid-state optically pure neutral S-(−)- and R-(+)-omeprazole.

DESCRIPTION OF THE INVENTION

Figure 1:
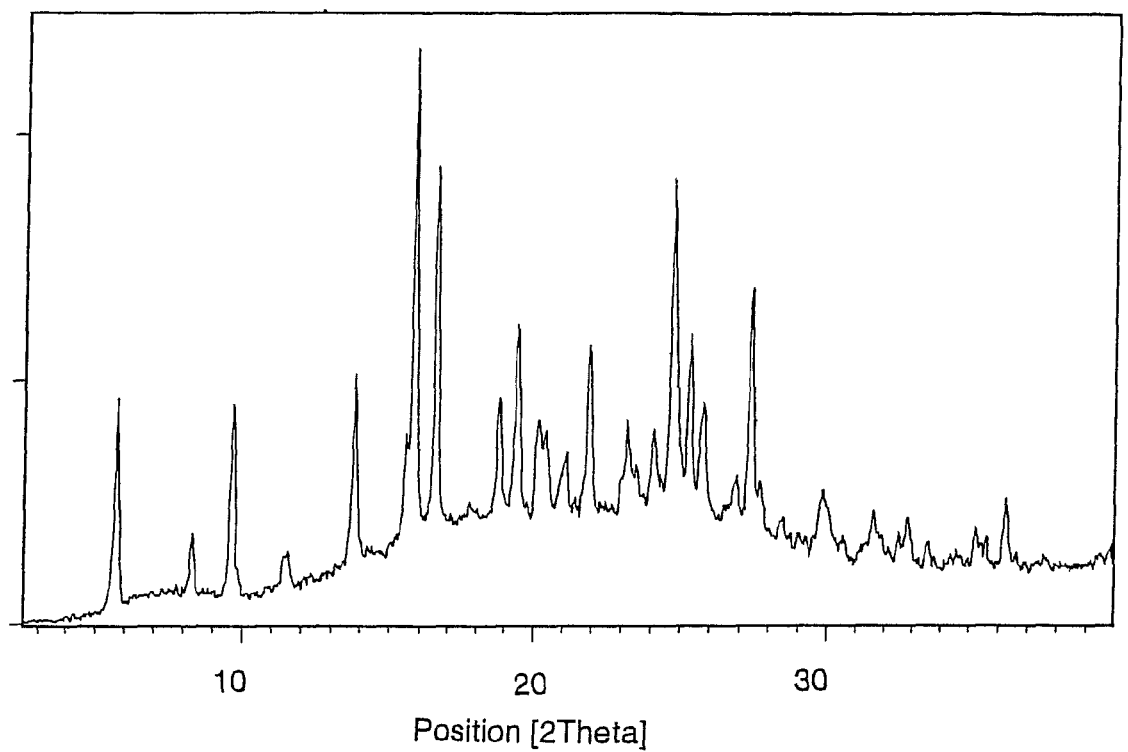
FIG. 1 is an X-ray powder diffractogram of esomeprazole non-salt modification B.

Various salts of the S-enantiomer of omeprazole, esomeprazole, can be crystallized, e.g. the sodium, potassium and magnesium salts, in a number of stable crystal modifications. Further, omeprazole (non-salt form) is crystalline and exists in several stable crystal modifications, but the non-salt form of esomeprazole is much more difficult to crystallize. Initially the non-salt form of esomeprazole was considered impossible to crystallize but eventually a number of crystal modifications have been found. A common problem with the previous processes is that they are difficult to control and often an amorphous lump may initially be formed before the crystallization starts. The present invention is an improved process for preparing the non-salt form of esomeprazole that overcomes the deficiencies of the earlier methods. The present invention improves the crystallization process and also increases the crystallinity of esomerazole non-salt modification B, compared to earlier processes. The improvements are achieved by the presence of an additional base in the essentially aqueous solution of esomeprazole non-salt form during crystallization. It has surprisingly been found that during the preparation of esomeprazole non-salt form in an essentially aqueous medium using said improved process, a number of novel crystal modifications are formed. Some of these novel crystal modifications are stable and thus possible to isolate, dry and characterize. Others are too short-lived to characterize and still others are only crystalline while in a damp and wet state, and are transformed into various amorphous forms upon drying and are, as a consequence, difficult to characterize. Further, it has also surprisingly been found that using the present improved process certain previously known crystal modifications can be produced with an improved (higher) crystallinity. Still other new crystal modifications are formed in the present process if performed at a temperature below ambient temperature. During the drying process all these modifications may pass through a number of additional forms with less crystalline content.

The process of the present invention renders possible the use of the novel crystal modifications and their properties, e.g. filtering properties, ease to handle, etc. The process of the present invention is thus more effective and efficient than those described in the art.

The present process is advantageous since it allows esomeprazole non-salt form to be prepared directly from a corresponding base addition salt, e.g. potassium salt, in high yield and in good quality. Additional merits are high reproducibility, good process ability including safety, in an environmentally friendly solvent like water.

The process of the present invention shows that it is possible to crystallize esomeprazole non-salt form in a controlled manner from the corresponding base addition salt, e.g. potassium salt, in an essentially aqueous system. This is accomplished by slowly adding an acid to an essentially aqueous solution of a base addition salt of esomeprazole, e.g. the potassium salt, and in the presence of an additional base. The addition rate of the acid shall be controlled, and preferably low, and by adding an additional base, such as an amine, to the system it is easier to control the crystallization rate. The present process thus effectively controls the rate of the pH change, i.e. the rate of supersaturation that directly translates into improved products of said process. The process of the present invention comprises the following steps:

i) Dissolving a base addition salt of esomeprazole in water containing at least one amine $B_1$;
ii) Adding at least one acid $HA_1$;
iii) Allowing esomeprazole non-salt form to crystallize and isolate the formed crystals.

In one embodiment of the present invention the amine $B_1$ is an organic amine or ammonia.

In one embodiment of the present invention the acid $HA_1$ is an organic acid or a mineral acid.

In one embodiment of the present invention the base addition salt of esomeprazole is esomeprazole potassium salt. Said esomeprazole potassium salt can be freshly prepared from the corresponding achiral sulphide and more or less immediately taken through the subsequent steps defined above. If so, the esomeprazole potassium salt can be prepared by any of the methods described in the prior art and thereafter dissolved in water containing an amine $B_1$.

In step ii) the pH is adjusted to produce esomeprazole in its non-salt form. This pH adjustment can be made by the addition of about less then 1 molar equivalents of a suitable acid $HA_1$, preferably 0.2-0.8 molar equivalents, more preferably 0.4-0.6 molar equivalents (relative to esomeprazole). The acid $HA_1$ is usually added as an aqueous solution.

Examples of such acid $HA_1$ comprises, but is not limited to, all acids that form water-soluble alkaline salts, e.g., citric acid, sodium bicarbonate, carbonic acid, hydrochloric acid, carbon dioxide, and acetic acid.

In another embodiment of the present invention esomeprazole sodium salt is used in step i) defined above.

The process of the present invention uses a controlled addition of acid $HA_1$ in combination with the presence of an amine $B_1$. This produces an improved control over the neutralization process compared to the processes of the prior art. Alternatively could an exorbitantly slow addition of the acid $HA_1$ to the base addition salt of esomeprazole in water without the presence of an amine $B_1$ be used to prepared the novel crystal modifications of the present invention. However, it is advantageous to use the process of the present invention since said process is more convenient, practical and gives a more controlled crystallization. The process of the present invention uses a less dilute solution, avoids initial lump formation of the esomeprazole non-salt form, and allows for faster addition of acid $HA_1$. The net result is thus a faster (less time consuming) and more reliable and up-scalable process.

All esomeprazole non-salt forms obtainable by the present process can be dried using conventional drying processes, as appropriate. The drying procedure actually used will slightly influence the position and intensities of the peaks in the X-ray diffractograms of esomeprazole non-salt forms B, C, E and G. In order to fully reproduce the diffractograms of FIG. 1 to 4 it is important to carefully follow the procedure of the Examples. Slight deviations therefrom may influence the position and intensities of the peaks in the X-ray diffractograms The amount of amine $B_1$ that remains in the formed non-salt forms is small. In most cases the amount is below 50 ppm, preferably below 20 ppm and even more preferably below 10 ppm.

For the avoidance of doubt it is to be understood that where in this specification a process step or similar activities is qualified by "hereinbefore defined", "defined hereinbefore" or "defined above" the step encompasses the first occurring and broadest definition as well as each and all of the other definitions for that step.

The phrase "more or less immediately" as used in the present specification is to be understood to mean that the subsequent step or action shall be performed at such a time to avoid degradation of the active compound. This subsequent step can thus be performed considerably later in time provided that due care has been taken to avoid degradation of the active compound.

Examples of suitable amines $B_1$ include, but is not limited to, ammonia, triethylamine, methylamine, ethylenediamine, ethanolamine, diethanolamine, trimethylamine, diethylamine and dimethylamine.

Another object of the present invention is to provide new stable crystal modifications of esoprazole non-salt form. Esomeprazole non-salt form can exist in more than one crystal modification. The crystal modifications or forms are hereinafter referred to as esomeprazole non-salt modifications B, C, E, and G. The notation B, C, E, and G relates to the order in time in which the crystal modification were invented, not to their relative thermodynamic stability.

It is an aspect of the present invention to provide esomeprazole non-salt modification C.

Figure 2:
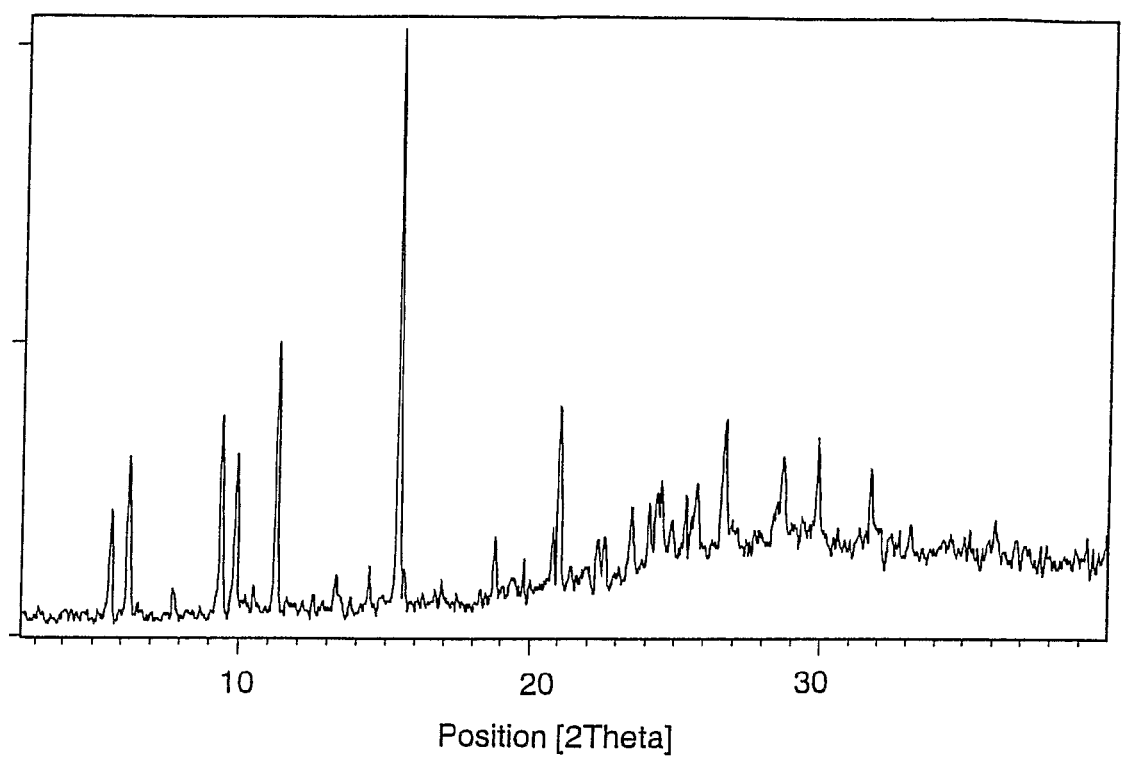
FIG. 2 is an X-ray powder diffractogram of esomeprazole non-salt modification C.

Esomeprazole non-salt modification C is characterized in providing an X-ray powder diffraction pattern, essentially as shown in FIG. 2.

It is a further aspect of the present invention to provide esomeprazole non-salt modification E.

Figure 3:
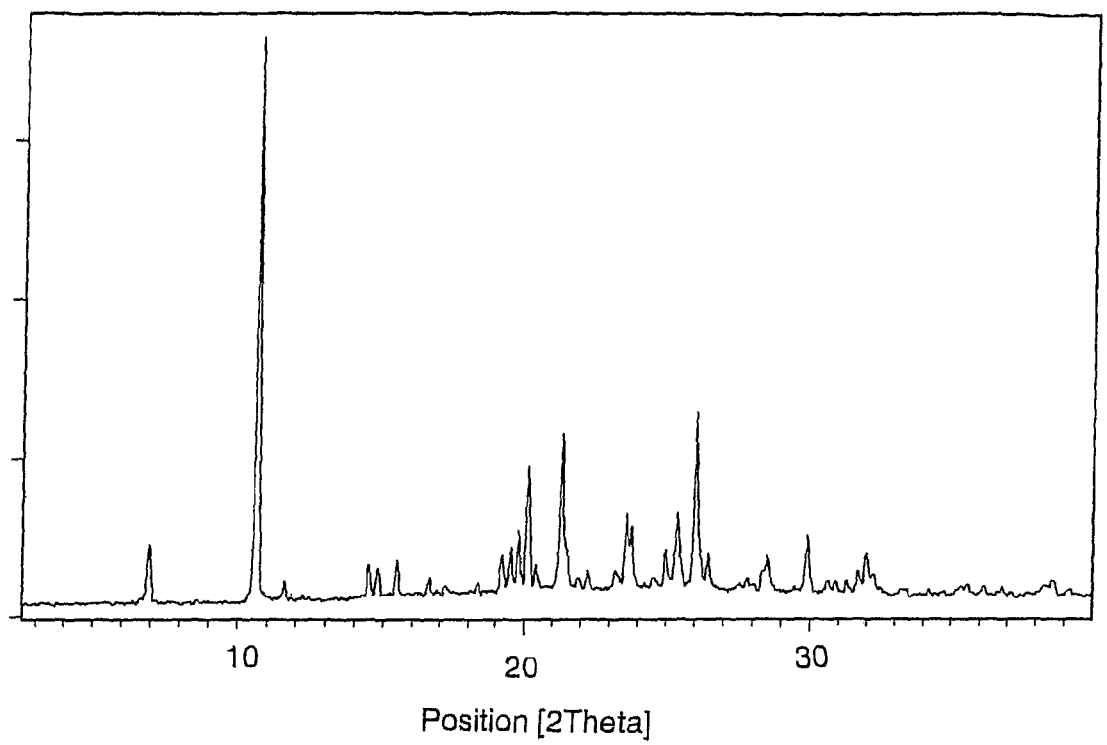
FIG. 3 is an X-ray powder diffractogram of esomeprazole non-salt modification E

Esomeprazole non-salt modification E is characterized in providing an X-ray powder diffraction pattern, essentially as shown in FIG. 3.

It is a further aspect of the present invention to provide esomeprazole non-salt modification G.

Figure 4:
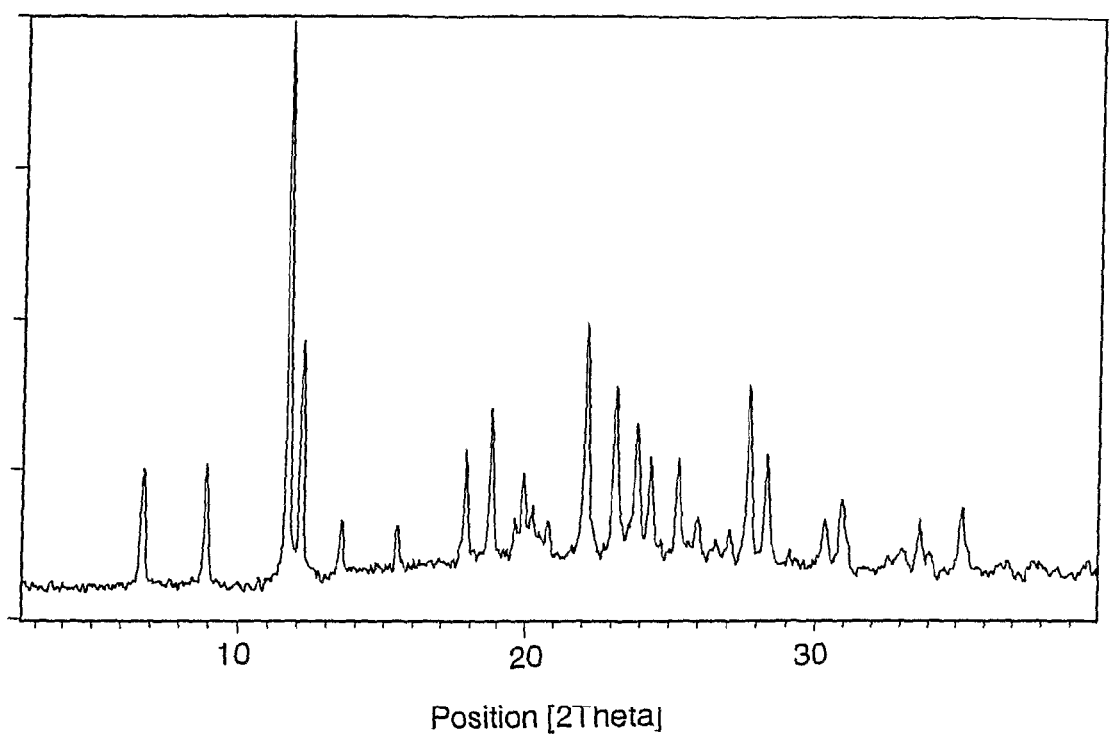
FIG. 4 is an X-ray powder diffractogram of esomeprazole non-salt modification G.

Esomeprazole non-salt modification G is characterized in providing an X-ray powder diffraction pattern, essentially as shown in FIG. 4.

It is an aspect of the present invention to provide an improved form of esomeprazole non-salt modification B. The improved form has a higher crystallinity compare to previous preparations. The improved crystallinity is shown by an improved signal-to-noise ratio in the X-ray powder diffractograms.

Esomeprazole non-salt modification B is characterized in providing an X-ray powder diffraction pattern, essentially as shown in FIG. 1.

In order to ensure that a particular crystal modification is prepared in the substantial absence of other crystal modifications, crystallization is preferably carried out by seeding. This applies particularly to each of the specific crystal modifications which are described in the Examples.

Esomeprazole non-salt modification B, C, E and G obtainable according to the present invention is substantially free from other crystal and non-crystal forms of esomeprazole non-salt form. The term "substantially free from other crystal and non-crystal forms of esomeprazole non-salt form" shall be understood to mean that the desired crystal form of esomeprazole non-salt contains less than 15%, preferably less than 10%, more preferably less than 5% of any other forms of esomeprazole non-salt form.

The crystal modifications of the present invention are effective as gastric acid secretion inhibitors, and are thus useful as antiulcer agents. In a more general sense, they can be used for prevention and treatment of gastric-acid related conditions in mammals and especially in man, including e.g. reflux esophagitis, gastritis, duodenitis, gastric ulcer and duodenal ulcer. Furthermore, they may be used for treatment of other gastrointestinal disorders where gastric acid inhibitory effect is desirable e.g. in patients on NSAID therapy, in patients with Non Ulcer Dyspepsia, in patients with symptomatic gastro-esophageal reflux disease, and in patients with gastrinomas. They may also be used in patients in intensive care situations, in patients with acute upper gastrointestinal bleeding, pre- and postoperatively to prevent aspiration of gastric acid, to prevent and treat stress ulceration and asthma, and for improvement of sleep. Further, the crystal modifications of the invention may be useful in the treatment of psoriasis as well as in the treatment of Helicobacter infections and related diseases. The crystal modifications of the invention may also be used for treatment of inflammatory conditions in mammals, including man.

Any suitable route of administration may be employed for providing the patient with an effective dosage of the esomeprazole non-salt form. For example, peroral or parenteral formulations, including i.v., and the like may be employed. Dosage forms include capsules, tablets, dispersions, suspensions, solutions and the like.

It is further provided a pharmaceutical composition comprising the crystal modifications of the present invention, as active ingredient, in association with a pharmaceutically acceptable carrier, diluent or excipient and optionally other active pharmaceutical ingredients. Compositions comprising other therapeutic ingredients are of interest in the treatment of the conditions listed above. The invention also provides the use of the crystal modifications in the manufacture of a medicament for use in said conditions as well as a method of treating a gastric-acid related condition which method comprises administering to a subject suffering from said condition a pharmaceutically effective amount of the crystal modifications.

The compositions of the invention includes compositions suitable for peroral or parenteral administration. The compositions may be conveniently presented in unit dosage forms, and prepared by any methods known in the art of galenic pharmacy.

In the practice of the invention, the most suitable route of administration as well as the magnitude of the therapeutic dose will depend on the nature and severity of the disease to be treated. The dose, and dose frequency, may also vary according to the age, body weight and response of the individual patient. Special requirements may be needed for patients having Zollinger-Ellison syndrome, such as a need for higher doses than the average patient. Children and patients with liver diseases generally will benefit from doses that are somewhat lower than average. Thus, in some conditions it may be necessary to use doses outside the ranges stated below, for example long-term treatments may request lower dosage. Such higher and lower doses are within the scope of the present invention. Such daily doses may vary between 5 mg to 300 mg.

In general, a suitable oral dosage form of the compound of the invention may cover a dose range from 5 mg to 300 mg total daily dose, administered in one single dose or equally divided doses. A preferred dosage range is from 10 mg to 80 mg.

The compound of the invention may be combined as the active component in intimate admixture with a pharmaceutical carrier according to conventional techniques, such as the oral formulations described in WO 96/01623 and EP 0 247 983, the disclosures of which are hereby as a whole included by reference.

Combination preparations comprising the compounds of the invention and other active ingredients may also be used. Examples of such active ingredients include, but are not limited to anti-bacterial compounds, non-steroidal anti-inflammatory agents, antacid agents, alginates and prokinetic agents.

The compounds of the invention may be further processed before formulation into a suitable pharmaceutical formulation. For example, the crystal modification may be milled or ground into smaller particles.

For the avoidance of doubt, "treatment" includes the therapeutic treatment, as well as the prophylaxis, of a condition.

The presence of additional substances in a sample, like pharmaceutical excipients, to be characterised by X-ray powder diffraction can mask some of the small peaks in any of the above characterized crystal modifications. This fact alone can of course not demonstrate that the crystal modification is not present in the sample. Under such circumstances due care must be used and the presence of substantially all main peaks in the X-ray powder diffraction pattern might suffice to characterize the crystal modification. It is thus preferred to analyse the crystal modifications of the present invention without the presence of additional substances.

Raman spectroscopy is an alternative method that can be used to characterize the crystal modifications of the present invention. Raman spectroscopy is further a technique that can be used to detect the presence of the crystal modifications of the present invention in admixture with pharmaceutical excipients.

The invention is illustrated, but in no way limited, by the following examples.

EXAMPLES

General Procedures

X-ray powder diffraction analysis (XRPD) was performed on samples prepared according to standard methods, for example those described in Giacovazzo, C. et al (1995), Fundamentals of Crystallography, Oxford University Press; Jenkins, R. and Snyder, R. L. (1996), Introduction to X-Ray Powder Diffractometry, John Wiley & Sons, New York; Bunn, C. W. (1948), Chemical Crystallography, Clarendon Press, London; or Klug, H. P. & Alexander, L. E. (1974), X-ray Diffraction Procedures, John Wiley and Sons, New York. X-ray diffraction analyses were performed using a Philips X'Pert MPD for 16 minutes from 1 to 40° 2θ. The samples were analyzed without internal reference since the addition may affect the time spent on preparation of the sample and thus influence the position and intensities of the peaks in the X-ray diffractograms. Measured peak values have been adjusted based on previous experiences (−0.05° 2θ). Calculation into d-values was done thereafter.

XRPD distance values may vary in the range ±2 on the last decimal place.

The majority of the examples below were performed in 5-10 g scale and corresponding 50-100 ml solution. The experiments were made either in conventional round flasks or in a small jacketed reactor coupled to a heating/cooling bath. Mixing was made by stainless steel, glass or Teflon impellers. Controlled addition of the acid for neutralization was obtained by using a Dosimat piston pump, which allows for constant addition rate. The starting material for the examples were esomeprazole potassium salt (assay 83.9% where the remaining 16.1% was methanol). The starting material was dissolved in water and then a small amount of amine was added. An acid was then added to the solution to decrease the pH from a start value of about 11-13 to about 8-9. pH value below about 8 shall be avoided. The solution was allowed to crystallize and the slurry was filtered off and washed with water. The samples were dried under vacuum and in most cases ambient temperature was used to avoid degradation. Extended drying generally gives amorphous material.

Example 1.1

Preparation of Esomeprazole Non-Salt Modification B

Esomeprazol-K (7.9 g) was dissolved in purified water (65 ml) at room temperature and aqueous ammonia (3.9 ml, 25%) was added. After this, 6.0 ml aqueous acetic acid (20%) was added slowly (0.0365 ml/min). The slurry was aged for one hour before more acetic acid was added (2.2 ml, 0.0365 ml/min). The slurry was left over night and before filtration, 80 ml water was added to dilute the slurry. The slurry was filtered off and washed with water (4×30 ml) and dried at 20° C. under vacuum over night.

Example 1.2

Preparation of Esomeprazole Non-Salt Modification C

Esomeprazol-K (7.84 g) was dissolved in purified water (65 ml) at room temperature and ammonia (aq), (3.9 ml, 25%) was added. The solution was cooled to 10° C. Aqueous acetic acid (25%) (6.56 ml) was added to the solution slowly (0.0365 ml/min). Seed crystals were added when 0.6 ml acid had been added to initiate crystallisation. The substance was allowed to crystallise for 2 hours at 10° C. Then, the slurry was filtered off and washed with water (3×20 ml) and dried in air. XRPD analysis showed a new form called modification C.

Example 1.3

Preparation of Esomeprazole Non-Salt Modification E

Esomeprazol-K (5.98 g) was dissolved in purified water (50 ml) at room temperature and ammonia (aq), (3 ml, 25%) was added. To the solution was added aqueous acetic acid (25%) (2.5 ml). Seed crystals were added to initiate crystallisation. The solution was heated to 30° C. and after 30 minutes more acetic acid was added (1.0 ml). The crystallisation started and larger lumps were formed, which gradually were transformed to a white slurry. After 3 hours more acetic acid was added (1.5 ml) and the resulting slurry was left over night. The crystals were then filtered off, washed with water and dried under vacuum and 20° C.

Example 1.4

Preparation of Esomeprazole Non-Salt Modification E

Esomeprazol-K (7.9 g) was dissolved in purified water (65 ml) at room temperature and ethanol amine (3.9 ml) was added. Aqueous acetic acid (20%) (8.5 ml) was slowly added to the solution (0.0365 ml/min). Seed crystals were added to initiate crystallisation. After this, 2.5 ml aqueous acetic acid (20%) was added in four portions every 30 minutes. Finally, the slurry was aged over night before, the slurry was filtered off and washed with water (3×30 ml) and dried at 25° C. under vacuum over night. The product (5.5 g) was a white, crystalline, powder.

Example 1.5

Preparation of Esomeprazole Non-Salt Modification G

Esomeprazol-K (7.89 g) was dissolved in purified water (65 ml) at room temperature and ammonia (aq), (3.9 ml, 25%) was added. Aqueous acetic acid (25%) (8.2 ml) was added to the solution slowly (0.0365 ml/min). Seed crystals were added to initiate crystallisation. The substance was allowed to crystallise for 3 days. Then, the slurry was filtered off and washed with water (2×30 ml) and dried at 25° C. under vacuum. XRPD analysis showed a new form called modification G.

Example 1.6

Preparation of Esomeprazole Non-Salt Modification G

Esomeprazol-K (7.9 g) was dissolved in purified water (35 ml) at room temperature. Diethanol amine (4.14 g) was mixed with 30 ml water and added to the Esomeprazol-K solution. Aqueous acetic acid (20%) (0.88 ml) was added to the solution (0.1 ml/min). Seed crystals were added to initiate crystallisation. After this, 7.32 ml aqueous acetic acid (20%) was added slowly (0.0365 ml/min). The slurry was aged over night before 0.5 ml acetic acid was added (20%, 0.1 ml/min), then 30 ml water was added and finally 1.5 ml aqueous acetic acid (20%, 0.1 ml/min)). The slurry was filtered off and washed with water (4×30 ml) and dried at 25° C. under vacuum over night yielding 6.1 g of modification G.

Example 1.7

Preparation of Esomeprazole Non-Salt Modification B

Esomeprazol-K (5.95 g) was dissolved in purified water (50 ml) at room temperature and methyl amine in ethanol (33%, 5 ml) was added. To the solution was added aqueous acetic acid (25%) (4.94 ml). After a few minutes, addition of 4.8 ml acetic acid (25%) was started. The acid was added in portions during 20 minutes. The crystallisation started spontaneously but lumps were formed. The temperature was increased to 30° C. during 10 minutes, then cooled down quickly to 10° C. and finally heated again to 25° C. After 4 hours at 25° C. more crystals were formed and the lumps were gradually transformed into a slurry which was left over night. The crystals were then filtered off, washed with water and dried under vacuum and 20° C.

The invention claimed is:

1. A process for preparing esomeprazole non-salt form comprising the following steps:
   i) dissolving a base addition salt of esomeprazole in water containing at least one amine $B_1$ selected from the group consisting of ammonia, triethylamine, methylamine, ethylenediamine, ethanolamine, diethanolamine, trimethylamine, diethylamine and dimethylamine;
   ii) adding at least one acid from selected from the group consisting of citric acid, sodium bicarbonate, carbonic acid, hydrochloric acid and acetic acid; and
   iii) allowing esomeprazole non-salt form to crystallize and isolating the formed crystals, wherein the esomeprazole non-salt form is selected from the group consisting of esomeprazole form B, esomeprazole form C, esomeprazole form E and esomeprazole form G.

2. The process according to claim 1, wherein the base addition salt is the potassium or sodium salt.

3. The process according to claim 1, wherein the pH after step ii) is about 8-9.

4. The process according to claim 1, wherein the amount of acid $HA_1$ added at step ii) is about 0.2-0.8 molar equivalents.

5. The process according to claim 1, wherein the acid is added as an aqueous solution.

6. The process according to claim 1, performed at ambient temperature.

7. The process according to claim 1, performed at about 10° C.

* * * * *

UNITED STATES PATENT AND TRADEMARK OFFICE
CERTIFICATE OF CORRECTION

| | |
|---|---|
| PATENT NO. | : 8,124,779 B2 |
| APPLICATION NO. | : 12/096199 |
| DATED | : February 28, 2012 |
| INVENTOR(S) | : Bohlin et al. |

It is certified that error appears in the above-identified patent and that said Letters Patent is hereby corrected as shown below:

<u>Col. 8</u>
Line 60 (claim 1): Insert --$HA_1$-- after --acid--.

Signed and Sealed this
First Day of May, 2012

David J. Kappos
*Director of the United States Patent and Trademark Office*